United States Patent [19]

Wevers

[11] Patent Number: 4,769,040
[45] Date of Patent: Sep. 6, 1988

[54] TIBIAL PROSTHESIS
[75] Inventor: Henk W. Wevers, Kingston, Canada
[73] Assignee: Queen's University at Kingston, Kingston, Canada
[21] Appl. No.: 931,856
[22] Filed: Nov. 18, 1986
[51] Int. Cl.$^4$ ............................................. A61F 2/38
[52] U.S. Cl. ................................................... 623/20
[58] Field of Search .................................... 623/16-23

[56] References Cited

U.S. PATENT DOCUMENTS

| 3,869,731 | 3/1975 | Waugh et al. | 623/20 |
| 4,340,978 | 7/1982 | Buechel et al. | 623/20 |
| 4,608,053 | 8/1986 | Keller | 623/23 |
| 4,662,888 | 5/1987 | Field | 623/23 |

FOREIGN PATENT DOCUMENTS

| 2845231 | 5/1979 | Fed. Rep. of Germany | 623/23 |
| 0611147 | 5/1979 | Switzerland | 128/92 YP |
| 0719625 | 3/1980 | U.S.S.R. | 623/20 |

Primary Examiner—Richard J. Apley
Assistant Examiner—David Isabella
Attorney, Agent, or Firm—Richard J. Hicks

[57] ABSTRACT

An improved tibial plateau prosthesis is described in which a baseplate is anatomically peripherally shaped and provided with a knife edge perimeter which cuts into the soft tissue outer edge of the epiphyseal shell of the tibia and effectively caps the tibia. Hoop stresses are reduced, and the use of wrought metal for the baseplate, inclusion of a deep intercondylar cut out as well as a series of perforations at locations corresponding to positions of hardness of the cancellous bone facilitates flexibility more in tune with the properties of the original subchondral bone plate and cartilage which in turn reduces "lift-off" from an unloaded condyle during loading of the other condyle. Bone ingrowth is encouraged by accurate flat cutting and the provision of the perforations. Initial stability is promoted by the knife edge and its asymmetrical circumferential shape.

9 Claims, 5 Drawing Sheets

LEGEND
○ CANCELLOUS BONE POST-OP
△ CORTICAL BONE POST-OP
□ CANCELLOUS BONE PRE-OP
● CORTICAL BONE PRE-OP

MALE TIBIAE

LEVEL 0mm  LEVEL 10mm

LEVEL 2.5mm  LEVEL 15mm

LEVEL 5mm  LEVEL 20mm

TIBIAL PROSTHESIS

FIELD OF INVENTION

This invention relates to a knee prosthesis and more particularly to a tibial plateau prosthesis.

BACKGROUND OF INVENTION

The bearing surfaces of the tibia and femur of the knee joint are vulnerable to stress, arthritic and other disease induced deterioration and it has become common practise to replace these bearing surfaces with prosthetic devices. These devices generally fall into three main types ranging from the relatively primitive hinge-type prosthesis to a somewhat more sophisticated ball and socket-type prosthesis to the now preferred, unconstrained rolling and sliding surface-type prosthesis in which the tibial and femoral components are unconnected. Typical of the hinge-type prosthesis is that shown by Lacey in U.S. Pat. No. 4,262,368 issued Apr. 21, 1981. An example of the ball and socket-type prosthesis is shown by Averill et al in U.S. Pat. No. 3,728,742 issued Apr. 24, 1973 and an example of the rolling surface-type is shown by Waugh et al in U.S. Pat. No. 3,869,731 issued Mar. 11, 1975. Attention is also directed to U.S. Pat. Nos. 3,816,855, 4,052,753, 4,404,691 and 4,224,696 which show various alternative forms of knee joint prostheses. The prior art has, however, paid scant attention to optimizing the design of the tibial component. Generally the tibial component has simplistically been considered as a substantially flat, symetrical plate against which the femoral component articulates, and this approach results in relatively poor life of the prosthesis, loosening of the tibial component due to bone necrosis beneath the prosthesis. The initial rigid fixation necessary for biological bone ingrowth is difficult to achieve because the epiphyseal shell is largely unrestrained in current prostheses, thus resulting in high shearloading during load-bearing. This, in turn, leads to micromovement loosening of the prosthesis and premature failure of originally good interfaces particularly when the prosthesis migrates, causing sinking of the medial side. This is compounded by the varus malalignment that is produced.

SUMMARY OF INVENTION

The present invention seeks to overcome the problems of the prior art by providing a total proximal tibial prosthesis which is designed to be relatively flexible in the axial direction and of controlled stiffness in the transverse direction and which resists hoop stresses in the epiphyseal shell during loading.

Thus by one aspect of the invention there is provided a proximal tibial prosthesis comprising a relatively thin, flexible baseplate having a circumferential shape corresponding substantially to the circumferential shape of a planar prepared surface of a proximal tibia and planar upper and lower surfaces, said circumferential shape on said lower surface being defined by a relatively thin, stiff metallic strip extending substantially perpendicularly from said lower surface; said baseplate having a structure so as to provide graduated flexibility in said baseplate corresponding to bone stiffness distribution in said proximal tibia; and a thermoplastic bearing surface plate having a peripheral shape corresponding to said baseplate and arrranged for mounting in overlying planar relationship on the upper surface thereof; said thermoplastic surface plate having an upper bearing surface adapted for articulation with a distal femoral prosthesis.

DETAILED DESCRIPTION OF PREFERRED EMBODIMENTS

Figure 1:
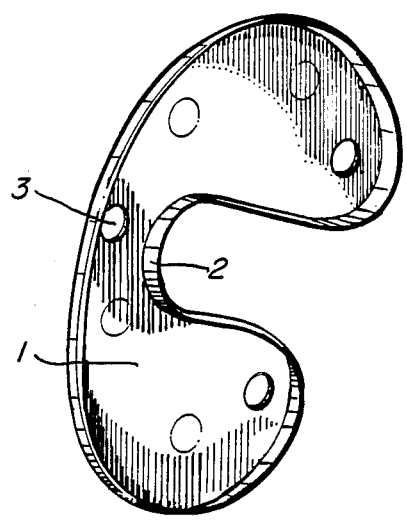
FIG. 1 is a perspective bottom view of one embodiment of the baseplate of the present invention (without perforations).

In the past it has been difficult to cut bony surfaces sufficiently flat to provide bone ingrowth between the prosthesis and the surgically prepared tibia. Bone ingowth in the tibia is particularly poor as it has been shown that only fibrous tissue is generally developed between the cancellous (or trabecular) bone and the porous metal surface. As it has been shown, however, that bone ingrowth can be made to occur when the porous metal surface is placed in close contact with bone and excessive micromovement avoided in the first 4-6 weeks of initial fixation, it would appear that failure of tibial bone ingrowth is due to either too much micromotion or insufficiently flat surgically prepared surfaces or a combination of both.

The anatomy of the tibia is very different between the medial and lateral side both geometrically and hystologically. The symmetry of most current prostheses is therefore only considered advantageous for economical reasons, namely to cut inventory at the manufacturing plant and in the hospital. This symmetry however is in contrast with the biologically evolved anatomical shape of the human proximal tibia. Medial articulation and loading is different from the lateral as shown by load models of the knee in different activities such as normal walking, stair climbing and rising from a chair. The shape of the articulating cartilage and the contact surface areas are also different for both condyles. For example, the medial compartment is 25% larger than the lateral side. In the complete joint the menisci also contribute very substantially to loadbearing. Furthermore, the cancellous bone strength of the proximal tibia is significantly different below the medial and lateral condyles, including the subchondral bone. As prostheses are usually positioned within the perimeter of the epiphyseal shell the medial side receives less coverage than optimal with a symmetric prosthesis, while the lateral side only, at best, is fully covered. This leads to a paradox, namely larger medial loading and less medial coverage.

All commercial tibia prostheses have a flat metal or HDPE face against the surgically cut cancellous bone of the proximal tibia. However, the pre-operative proximal tibia has a unique structure which is physiologically adapted for loadbearing. Histological study of the cancellous bone architecture in general, and of the mechanical properties of the epiphyseal shell and the subchondral bone, revealed an integrated "assembly" with all three areas interacting to support local loading at the articulating surface and to transfer the load from there to the distal cortical shaft.

Computer modelling has confirmed the adaptation of tissues to loadbearing and load transfer in the proximal tibia. Removing the subchondral plate surgically exposes a "decapitated" cancellous bone which was structurally designed to withstand axial loading while laterally supported by an epiphyseal shell. The "decapitated" configuration can no longer interact with the subchondral bone plate and has therefore lost its anchoring by the subcondral plate. This biological anchor resisted hoop stresses that normally occur during articulation.

To determine an anatomically shaped periphery for the prosthesis thirty-two randomly selected tibiae of the Caucasian race were photographed in the direction of the long axis and the perimeter was digitized. The anatomy of the tibia is such that its perimeter is equal or close to the circumference of the exposed cancellous bone surface prior to insertion of the prosthesis. The perimeter data were normalized for width and the geometric deviations were assessed. As average profile was then developed by minimizing the geometric deviations and it has been used as the "average anatomical circumference" for the prosthesis. From the width variation, which was distributed according to a Gaussion normal distribution, and the correlation that exists between the width, depth and other geometric features a series of 3 and 5 sizes were developed. Each one of the 32 previously randomly selected tibiae was then "fitted" with the best average anatomical geometry of the size series and a percentage coverage was calculated.

Histological studies showed that the bone structure of the epiphyseal shell consists of a cancellous bone shell with a thickness equal to trabeculae abutting the wall. The wall is further reinforced by collagen fibres wrapped around the epiphyseal shell in the hoop direction. This pattern was interrupted in the areas of ligament and synovial membrane attachments.

Cancellous bone support is evidenced by relative high stresses of up to 3.26 MPa just under the loadbearing areas. The cancellous bone most proximally carries all the load while the epiphyseal shell and distal cortex gradually share the load-bearing. At level 5 FIG. 5, or a distance of approximately 20 mm below the subchondral plate, cancellous bone and cortical bone bear equal load. After this cross-over point the cortex is increasingly loadbearing.

Figure 5:
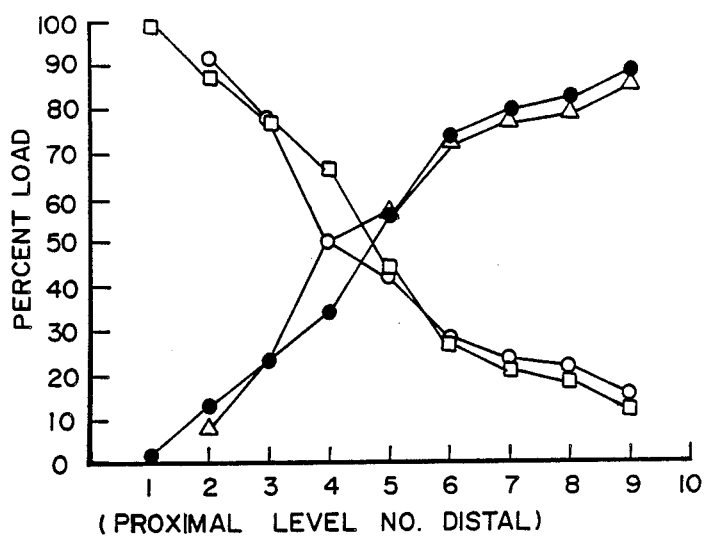
FIG. 5 is a graph illustrating loadbearing cancellous and cortical bone in pre and post-operative models.

In the post-operative PCA model, compressive surface stresses of up to 7.5 MPa are more evenly distributed and the hoop stresses are small (at less than 2.5 MPa) possibly due to the rigid radial constraint by the prosthesis. Compressive stresses in the coronal section are very low in the cancellous bone with stress concentrations up 20 MPa at the PCA pegs. Loadsharing between cancellous bone and the epiphyseal shell and cortex is shown in FIG. 5. As can be noted, the crossover point for loadsharing between cancellous and cortical bone is at level 4 or approximately 16 mm distally from the subchondral bone.

Figure 2:
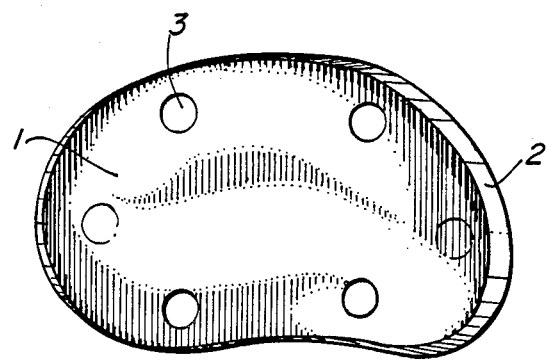
FIG. 2 is a perspective bottom view of an alternative embodiment of the baseplate of the present invention (without perforations).

The anatomical geometry and the biomechanical analysis have been combined in a new tibial prosthesis shown in FIGS. 1 and 2.

As may be seen, FIG. 1 shows a baseplate 1 peripherally shaped to conform anatomically with a surgically prepared proximal tibia, and provided with a peripheral rim 2 extending substantially perpendicularly downwardly (when in operative orientation) from the plate 1. Preferably baseplate 1 is fabricated in metal, but reinforced polymeric materials are also contemplated. Rim 2 is preferably knife-edge so as to cut through the soft tissue outer part of the epiphyseal shell when it is implanted. FIG. 1 shows an ana-tomical shape designed for retention of the posterior cruciate ligament. If the cruciate ligament is not to be retained, then the design shown in FIG. 2, in which the deep intercondylar cutout is omitted, may be used. The baseplates may be fabricated by diepunching, forging or by deepdrawing in cobalt-chromium (ASTMF799) or titanium (ASTFM136) alloys or other suitable alloys or plastics.

Figure 3:
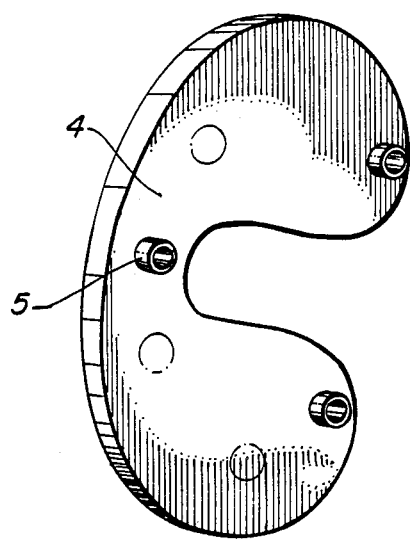
FIG. 3 is a perspective bottom view of the bearing surface plate for use with the embodiment of FIG. 1.
Figure 4:
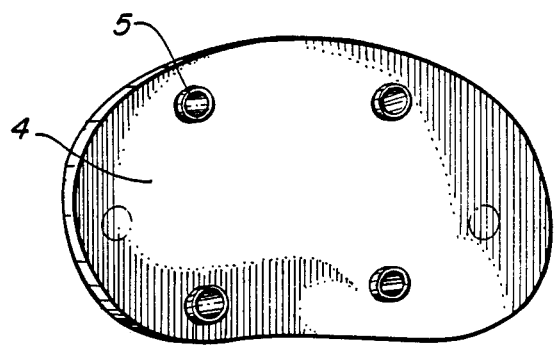
FIG. 4 is a perspective bottom view of the bearing surface plate for use with the embodiment of FIG. 2.

The upper articulating surface of the prosthesis is provided by a high density polyethylene (HDPE) section appropriately peripherially contoured as shown in FIGS. 3 and 4 for use with the baseplates 1 shown in FIGS. 1 and 2 respectively. The lower side of HDPE section 5 is provided with three or four metal locating pins 5 arranged to be received through holes 3 in the baseplate 1. The pins 5 should be made of the same material as baseplate 1 and are preferably laterally perforated to allow for bone ingrowth. The articulating surface of the section 4 is contoured to interact in a modular fashion with a selected, currently available femoral prosthesis such as the Townley or PCA (Howmedica).

Figure 6:
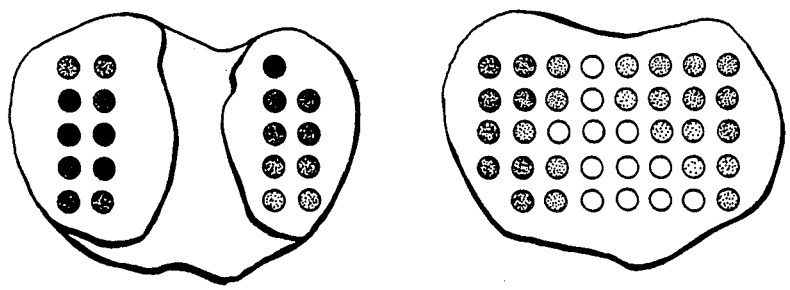
FIG. 6 is a sketch of various hardness profiles of the tibia.
Figure 6:
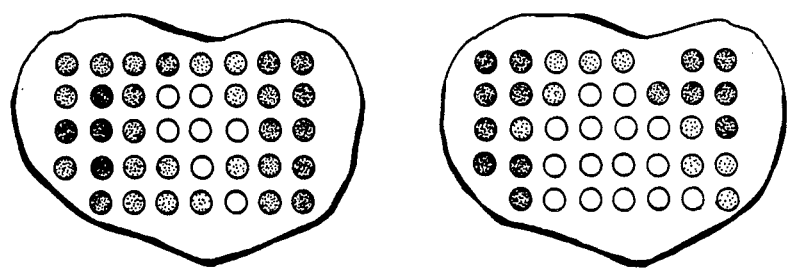
Figure 6:
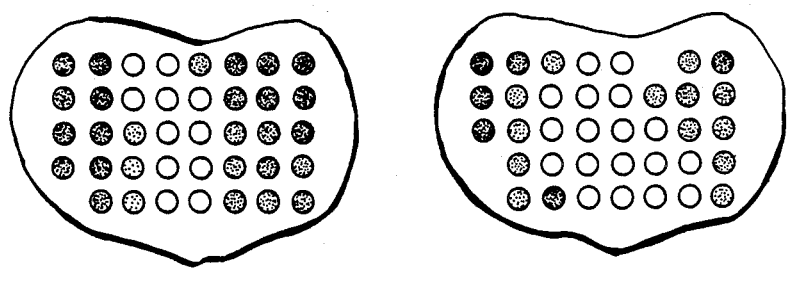
Figure 6:
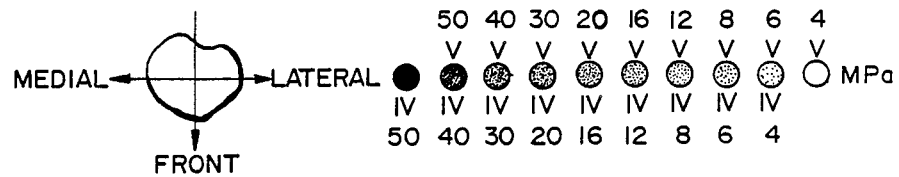
Figure 7A:
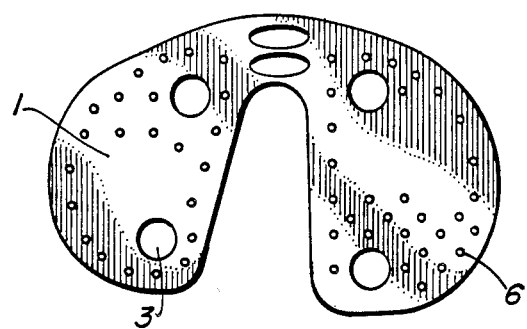
FIG. 7(a) and (b) are plain views of left and right tibial baseplates, with perforations, according to the embodiment of FIG. 1.
Figure 7B:
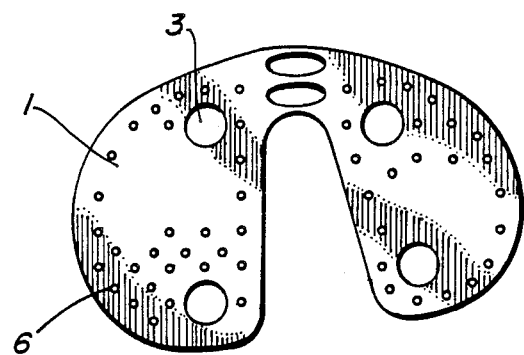

In experimental fitting of one of the average anatomical shapes from the series of 3 or 5, coverage of 90.3% (standard deviation of 4%) achieved with the size series of 3 and 92.4% (standard deviation of 2.5%) with the 5 size series. The medial and lateral condyle can act largely independently when loaded differently in the axial direction, thus reducing lift-off stress. The knife edge caps the tibia and restores radial support for the epiphyseal shell. The stiffness of the baseplate can be controlled by perforating in the case of metal baseplates or by appropriately reinforced areas in the case of polymeric baseplates and loadbearing can be directed to the areas of hard proximal cancellous bone with the aim of physiological transfer of compressive stresses to the distal cortex. Areas of hard cancellous bone are shown in FIG. 6. The perforations 6 in the tibial metal bone plate are intended to align with the area of cancellous bone hardness, the largest number of perforations will be in the areas of weak cancellous bone as shown in FIGS. 7(a) and 7(b) representing left and right tibial baseplates respectively. The metal perforations also form crevices for bone ingrowth or for anchoring by PMMA bone cement. Similar perforations in the knife edge promote tissue ingrowth which in turn stabilizes the prosthesis in tension.

It will be appreciated by those skilled in the art that the tibial plateau design of the present invention has taken into account the physiological structure and the cancellous bone hardness pattern of the tibia so that post-operative loadbearing is improved. Micromovement in the radial direction is minimized by the capping of the tibia as the epiphyseal shell is radially supported by the metal knife edge. The intercondylar cutout (in the embodiment of FIGS. 1 and 3) provides for extra fixation by preserving the intercondylar notch which in turn further reduces lift-off of the unloaded condyle during loadbearing of the opposite condyle. Physiologically preferred flexion is also facilitated by use of a wrought metal rather than a relatively thick and brittle casting as in the prior art. The perforations allow for firm mechanical anchoring by PMMA cement or by bone ingrowth without the accom-panying problem of metal fragment loosening which has been described in the literature.

I claim:

1. A tibial prosthesis comprising a relatively thin, flexible baseplate anatomically peripherally shaped to conform to a planar prepared surface of a proximal tibia, having planar parallel opposed upper and lower surfaces and a relatively thin, stiff peripheral rim extending continuously around said baseplate and substantially perpendicularly from said planar lower surface and arranged so as to constrain hoop stresses in said proximal tibia and provide initial fixation against rotation about a long axis of the tibia and shear perpendicular to said long axis; said baseplate being arranged to provide graduated flexibility in said baseplate corresponding to bone stiffness distribution in said tibia; and a relatively thin thermoplastic planar bearing plate peripherally conforming to said baseplate, arranged for mounting in overlying planar relationship to said upper surface and having a planar upper bearing surface adapted for articulation with a distal femoral prosthesis.

2. A prosthesis as claimed in claim 1 wherein said peripheral rim is provided with a plurality of perforations.

3. A tibial prosthesis comprising a relatively thin, flexible metallic baseplate anatomically peripherally shaped to conform to a planar prepared surface of a proximal tibia, having planar parallel upper and lower opposed surfaces and a relatively thin, stiff, metallic peripheral rim extending continuously around said baseplate and substantially perpendicularly from said lower planar surface and arranged so as to constrain hoop stresses in said proximal tibia and provide initial fixation against rotation about a long axis of the tibia and shear perpendicular to said long axis; said baseplate being perforated by a plurality of spaced holes arranged to provide graduated flexibility in said baseplate corresponding to bone stiffness distribution in tibia; and, a relatively thin thermoplastic planar bearing plate peripherally conforming to said metallic baseplate, arranged for mounting in overlying planar relationship thereto and having a planar bearing surface adapted for articulation with a distal femoral prosthesis.

4. A prosthesis as claimed in claim 3 wherein said peripheral rim is also provided with a plurality of perforations.

5. A prosthesis as claimed in claim 3 wherein said metallic baseplate is a cobalt-chromium or titanium alloy.

6. A prosthesis as claimed in claim 5 wherein said thermoplastic plate is a high density polyethylene plate.

7. A prosthesis as claimed in claim 1 wherein said baseplate and said bearing plate include an intercondylar slot.

8. A prosthesis as claimed in claim 3 wherein said baseplate and said bearing plate include an intercondylar slot.

9. A prosthesis as claimed in claim 1 wherein said baseplate is a reinforced polymeric baseplate.

* * * * *